(12) United States Patent
Therianos et al.

(10) Patent No.: US 10,246,748 B2
(45) Date of Patent: Apr. 2, 2019

(54) BIOMARKER COMBINATIONS FOR COLORECTAL TUMORS

(71) Applicant: Novigenix SA, Epalinges (CH)

(72) Inventors: Stavros Therianos, Lausanne (CH); Curzio Ruegg, Marly (CH); Sylvain Monnier-Benoit, Malbuisson (FR); Laura Ciarloni, Lausanne (CH); Sahar Hosseinian, Epalinges (CH)

(73) Assignee: NOVIGENIX SA, Epalinges (CH)

( * ) Notice: Subject to any disclaimer, the term of this patent is extended or adjusted under 35 U.S.C. 154(b) by 0 days.

(21) Appl. No.: 14/440,850

(22) PCT Filed: Nov. 4, 2013

(86) PCT No.: PCT/EP2013/072965
§ 371 (c)(1),
(2) Date: May 5, 2015

(87) PCT Pub. No.: WO2014/068124
PCT Pub. Date: May 8, 2014

(65) Prior Publication Data
US 2015/0299802 A1  Oct. 22, 2015

(30) Foreign Application Priority Data
Nov. 5, 2012 (EP) .................................. 12191236

(51) Int. Cl.
*C12Q 1/68* (2018.01)
*C12Q 1/6886* (2018.01)
*G06F 19/12* (2011.01)
*G06F 19/20* (2011.01)
*G16H 50/20* (2018.01)

(52) U.S. Cl.
CPC ........... *C12Q 1/6886* (2013.01); *G06F 19/12* (2013.01); *G06F 19/20* (2013.01); *G16H 50/20* (2018.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2009/0215053 A1  8/2009  Galon et al.
2010/0196889 A1  8/2010  Bankaitis-Davis et al.

FOREIGN PATENT DOCUMENTS

| RU | 2 410 438 C2 | 1/2011 |
| WO | WO-2006/017859 A2 | 2/2006 |
| WO | WO-2006/017859 A3 | 2/2006 |
| WO | WO-2009/037572 A2 | 3/2009 |
| WO | WO-2009/037572 A3 | 3/2009 |

OTHER PUBLICATIONS

Sano et al (Cancer Research, 1995, 55: 378-3789).*
Maihofner et al (Carcinogenesis, 2003, 24(4): 665-671).*
Kim et al (Journal of Proteome Research, 2009, 8: 1368-1379).*
Etzioni et al (Nature Reviews, Apr. 2003, 3: internet pp. 1-10).*
Mercer (Immunol Ser, 1990, 53:39-54).*
Moore et al (Gynecologic Oncology, 2008, 108: 402-408).*
O'Connell (Oncology, 2004, 18(6): 751-755).*
Watanabe et al (Clin Cancer Res, 2007, 13(2): 415-420).*
Huang et al (Journal of the National Medical Association, 2008, 100(12): 1425-1433).*
Pilarsky et al (J Cell Mol Med, 2008, 12(6B): 2823-2835).*
Sipos et al (Disease Markers, 2011, 30: 1-17).*
DePrimo et al (BMC Cancer, 2003, 3(3): 1-12).*
Booken et al (Leukemia, 2008, 22: 393-399).*
Duque, J. et al. (Aug. 2006, e-published Dec. 2, 2005). "Up-regulation of cyclooxygenase-2 by interleukin-1beta in colon carcinoma cells," *Cell Signal* 18(8):1262-1269.
Jemal, A. et al. (Jul.-Aug. 2009, e-published May 27, 2009). "Cancer Statistics, 2009," *CA Cancer J Clin* 59(4):225-249.
Liu, W. et al. (Jul. 2003). "Cyclooxygenase-2 is up-regulated by interleukin-1 beta in human colorectal cancer cells via multiple signaling pathways," *Cancer Research* 63913):3632-3636.
International Search Report dated Jan. 17, 2014, for PCT Application No. PCT/EP2013/072965, filed Nov. 4, 2013, 6 pages.
Written Opinion dated Jan. 17, 2014, for PCT Application No. PCT/EP2013/072965, filed Nov. 4, 2013, 6 pages.
Maihofner, C. et al. (Apr. 2003). "Expression of cyclooxygenase-2 parallels expression of interleukin-1beta, interleukin-6 and NF-kappaB in human colorectal cancer," *Carcinogenesis* 24(4):665-671.

* cited by examiner

*Primary Examiner* — Sean E Aeder
(74) *Attorney, Agent, or Firm* — Mintz Levin Cohn Ferris Glovsky and Popeo P.C.

(57) ABSTRACT

The present invention relates to methods and kits for the detection of predetermined biomarkers for early diagnosis and management of cancer, and in particular, colorectal tumors.

24 Claims, 3 Drawing Sheets
Specification includes a Sequence Listing.

SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
acaacaacct acggcagaca                                           20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ccacagacgg taatgtggtg                                           20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tccaagcaca gctatctcct t                                         21

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ccctctttca ccagccttc                                            19

```
<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
agtgatttcc acagtgactc ca                                              22

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggcagatgct ggctactgat                                                 20

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gaatgaaatg tgtgaagttc ttgc                                            24

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gcaatcagtc ccactgcac                                                  19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
caggagtttg gctggttgat                                                 20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
cagttgccct tcggagagt                                                  19

<210> SEQ ID NO 11
<211> LENGTH: 23
<212> TYPE: DNA
<213> ORGANISM: Artificial Sequence
<220> FEATURE:
<223> OTHER INFORMATION: Primer
```

<400> SEQUENCE: 11
aaaaggtatg caatcaaatc tgc                                                    23

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
aagaatttgg gccccttg                                                          18

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
ttgtgtgcta cagttgttca agg                                                    23

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tctgccactt tcactgcttt ta                                                     22

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
accacaagca ccaaagcag                                                         19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ggcgtcattt agcacttggt                                                        20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
agcacctgac cgcagagt                                                          18

<210> SEQ ID NO 18
<211> LENGTH: 18

```
<212> TYPE: DNA
<213> ORGANISM: Artificial Sequence
<220> FEATURE:
<223> OTHER INFORMATION: Primer

<400> SEQUENCE: 18
ggcagtcgag tggtttgg                                                    18

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
accacgtcca gttcttcagc                                                  20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gggctggagt tctgtgtaga ct                                               22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cacaagatga atgggcagaa                                                  20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
tgacaatttg cacaacaggt g                                                21

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
agctgatggc cctaaacaga                                                  20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
```

```
tcggagattc gtagctggat                                            20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tagccaggat ccacaagtcc                                            20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ctgtgaggta agatggtggc ta                                         22

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
aacatgagcc tcggcttg                                              18

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
gcccacagag gaccacat                                              18

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
gcatgcagca ccaagagag                                             19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gcaggtctgg ttgtcaggtt                                            20

<210> SEQ ID NO 31
<211> LENGTH: 22
<212> TYPE: DNA
<213> ORGANISM: Artificial Sequence
```

```
<220> FEATURE:
<223> OTHER INFORMATION: Primer

<400> SEQUENCE: 31
agtcaggcag acagacagac ac                                          22

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
aaaataagat ttgcagttcg gactat                                      26

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
taaggtggaa cgcctgaaac                                             20

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
ccatttctcc caaatttagc c                                           21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
cgagtttgtg gacttcactg c                                           21

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
aaggtgaaga agggtgctc                                              20

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
tggatgaaac tcacagtcac att                                         23
```

```
<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
ggccaatcat gctctgaaa                                                19

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
aagaggttcg tgctttctgg                                               20

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
ccatgggaac cgaaggat                                                 18

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
atccggcacc tctatggtc                                                19

<210> SEQ ID NO 42
<211> LENGTH: 16
<212> TYPE: DNA
<213> ORGANISM: Artificial Sequence
<220> FEATURE:
<223> OTHER INFORMATION: Primer

<400> SEQUENCE: 42
cagaccgtcg ggggag                                                   16

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
caggccaagg aaaaggagat                                               20

<210> SEQ ID NO 44
<211> LENGTH: 18
<212> TYPE: DNA
<213> ORGANISM: Artificial Sequence
<220> FEATURE:
<223> OTHER INFORMATION: Primer
```

-continued

<400> SEQUENCE: 44
cgttcaatcc gagcaagg                                                 18

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cctaagcagc tggaaggaac                                               20

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
cgcttgataa tctctcccac a                                             21

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
gacaggaaag acaacagaca aatc                                          24

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
ggggtgatgt gtttgaactt g                                             21

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
agaaggcctt tgccaacc                                                 18

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gatggtctcc atgtcgttcc                                               20

<210> SEQ ID NO 51

```
<211> LENGTH: 18
<212> TYPE: DNA
<213> ORGANISM: Artificial Sequence
<220> FEATURE:
<223> OTHER INFORMATION: Primer

<400> SEQUENCE: 51
cgctcagcca tacagcaa                                                   18

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
tcatacatac acctcggttt tga                                             23

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
agcacaccag gagagagctg                                                 20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gtagccaaag gcactgatcc                                                 20

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
cagctgtctt tcagaagacc tg                                              22

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ctttctccag ctcggtcaac                                                 20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
```
ctcaagactg cttgcaactg a                                              21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
aagctgagaa gccatggaac                                                20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
tgctacagag caggagttgc                                                20

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
tcctgttctt caagctctgg t                                              21

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tcgacaatgg cagcatctac                                                20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
gccaatctgc agacagacac                                                20

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
caatcaaagg gaaacttgaa gaa                                            23

<210> SEQ ID NO 64
<211> LENGTH: 26
<212> TYPE: DNA

```
<213> ORGANISM: Artificial Sequence
<220> FEATURE:
<223> OTHER INFORMATION: Primer

<400> SEQUENCE: 64
gattcatgtt ttcaccaata aagaac                                              26
```

BIOMARKER COMBINATIONS FOR COLORECTAL TUMORS

RELATED APPLICATIONS

The present application is a national stage application, filed under 35 U.S.C. § 371, of International Application No. PCT/EP2013/072965, filed on Nov. 4, 2013, which claims priority, and benefit to the EP Application No. 12191236.4 filed Nov. 5, 2012, the contents of which are incorporated herein by reference in their entireties.

INCORPORATION-BY-REFERENCE

The contents of the text file named "36522-502001WO_ST25.txt", which is created on Oct. 30, 2013 and is 11.5 KB in size, are hereby incorporated by reference in their entireties.

FIELD OF THE INVENTION

The present invention relates generally to peripheral blood biomarkers related to colorectal tumors, and methods of use thereof.

BACKGROUND OF THE INVENTION

Worldwide, colorectal cancer (CRC) is the third most common cancer, following lung and breast cancer and leading cause of 650,000 cancer related deaths per year (Jemal, A., Siegel, R., Ward, E., Hao, Y., Xu, J., Thun, M. *Cancer Statistics* 2009. *CA Cancer J Clin* 2009; 59; 225-249). In Europe, it is the second largest form of cancer and the second largest cause of death, following lung cancer. However, the CRC screening rates remain suboptimal (~20%) and lag far behind those for breast, cervical and prostate cancer.

Thus, there is urgent need for new and more compliant screening method for CRC.

SUMMARY OF THE INVENTION

The present invention relates to biomarkers and relative methods for screening, detecting, diagnosing and monitoring colorectal tumors.

The present invention provides a method that includes the steps of (a) measuring in a sample obtained from a subject the amount of each biomarker of a biomarker panel including at least one high priority biomarker and at least two core biomarkers selected from the group consisting of IL1B, PTGS2, S100A8, LTF, CXCL10 and CACNB4; (b) (b) calculating a probability score based on the measurement of step (a); and (c) ruling out colorectal tumor for the subject if the score in step (b) is lower than a pre-determined score; or ruling in the likelihood of colorectal tumor for the subject if the score in step (b) is higher than a pre-determined score. The likelihood of colorectal tumor can further be determined by the sensitivity, specificity, negative predictive value (NPV) or positive predictive value (PPV) associated with the score.

The present invention also provides a method that includes the steps of (a) measuring in a sample obtained from a subject the amount of each biomarker of a biomarker panel including at least one high priority biomarker and at least two core biomarkers selected from the group consisting of IL1B, PTGS2, S100A8, LTF, CXCL10 and CACNB4; (b) comparing the amount measured in step (a) to a reference value; and (c) classifying the subject as more likely to have colorectal tumor when an increase or a decrease in the amount of each biomarker of the biomarker panel relative to the reference value is detected in step (b). The method may further include a step of administering to the subject classified by step (c) a therapeutically effective amount of at least one colorectal-modulating agent.

In certain embodiments, the at least one high priority biomarker is selected from the group consisting of S100A8, LTF, CXCL10 and CACNB4.

In certain embodiments, the at least one high priority biomarker is selected from the group consisting of S100A8, LTF, CXCL10, CACNB4, MMP9, CXCL11, EGR1, JUN, TNFSF13B, GATA2, MMP11, NME1, PTGES, CCR1, CXCR3, FXYD5, IL8, ITGA2, ITGB5, MAPK6, RHOC, BCL3, CD63, CES1, MAP2K3, MSL1, and PPARG.

In certain embodiments, the at least two core biomarkers are IL1B and PTGS2.

In certain embodiments, the at least two core biomarkers are (a) IL1B and PTGS2; (b) IL1B, PTGS2 and S100A8; (c) IL1B, PTGS2, S100A8 and LTF; (d) IL1B, PTGS2, S100A8, LTF, and CXCL10; or (e) IL1B, PTGS2, S100A8, LTF, CXCL10 and CACNB4.

In certain embodiments, when colorectal tumor is ruled out the subject does not receive a treatment protocol.

In certain embodiments, when colorectal tumor is ruled in the subject receives a treatment protocol. For example, the treatment protocol is a colonoscopy, a biopsy, a surgery, a chemotherapy, a radiotherapy, or any combination thereof.

In certain embodiments, the probability score can be calculated from a logistic regression prediction model applied to the measurement.

The sample may be peripheral blood mononuclear cells, blood cells, whole blood, serum, plasma, endothelial cells, circulating tumor cells, tissue biopsies, lymphatic fluid, ascites fluid, interstitial fluid, bone marrow, cerebrospinal fluid (CSF), saliva, mucous, sputum, sweat or urine.

In certain embodiments, the colorectal tumor is adenoma or carcinoma.

In certain embodiments, the subject is at risk of developing colorectal tumor.

The invention also provides a kit to be used according to the aforementioned method for detecting the presence of colorectal tumors. The kit comprises one or more than one primer pair for measuring one or more biomarker, particularly the panel of biomarkers as described herein (Table 1).

The kit may further comprise one or more probes, reference samples for performing measurement quality controls, plastic containers and reagents for performing test reactions and instructions for using the reagents in the method of any one of the preceding claims.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from the following detailed description and claims.

BRIEF DESCRIPTION OF THE DRAWINGS

The following Detailed Description, given by way of example, but not intended to limit the invention to specific embodiments described, may be understood in conjunction with the accompanying figure, incorporated herein by reference, in which.

DETAILED DESCRIPTION

Figure 1:
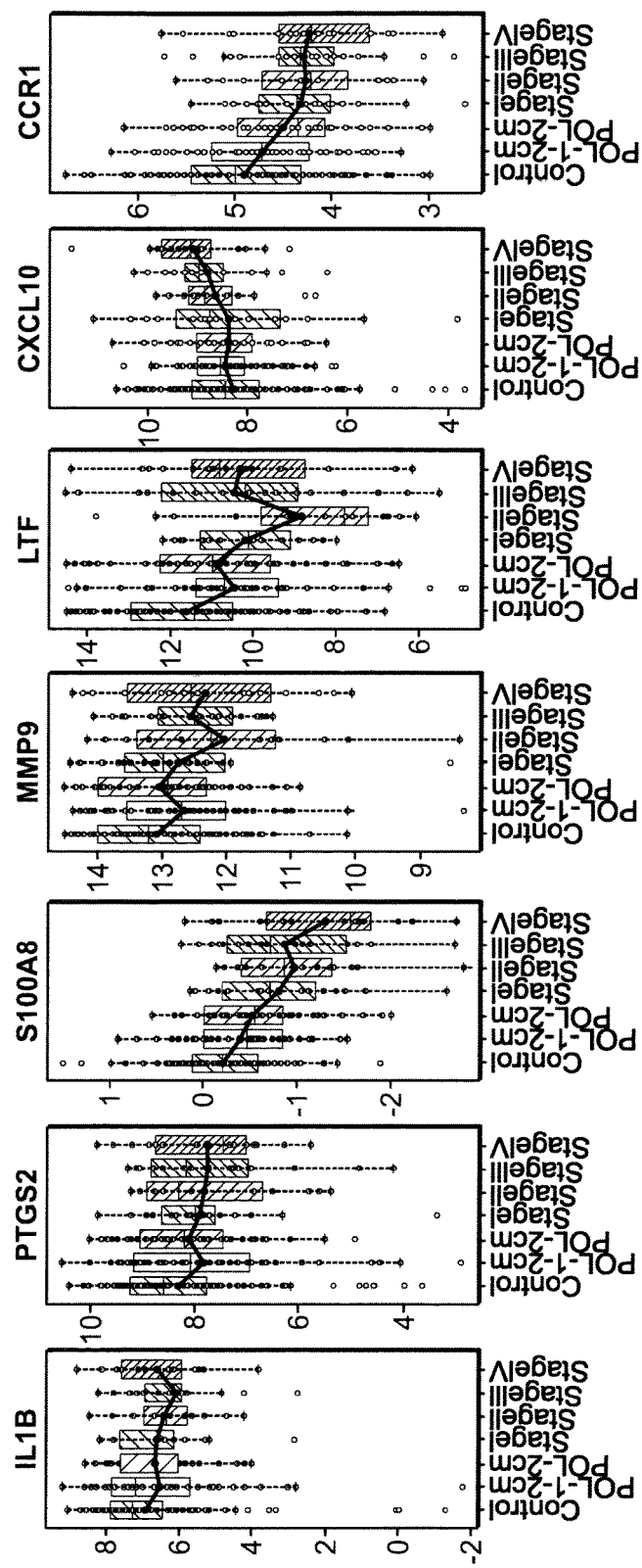
FIG. 1. Boxplots depict IL1B, PTGS2, S100A8, MMP9, LTF, CXCL10 and CCR1, gene expression during colorectal cancer evolution and progression: controls, adenomas (POL) between 1-2 cm, adenomas greater than 2 cm and carcinomas stage I to IV. Measurement unit correspond to deltaCp values. To be noted that different unit scales were used for different gene graphs.

The present invention is partially based upon the discovery that a small panel of biomarkers in the blood is able to specifically identify and distinguish subjects with malignant and benign colorectal lesions from subject without such lesions.

Accordingly, the invention provides unique advantages to the patient associated with early detection of colorectal tumor in a patient, including increased life span, decreased morbidity and mortality, decreased exposure to radiation during screening and repeat screenings and a minimally invasive diagnostic model. Importantly, the methods of the invention allow for a patient to avoid invasive procedures, thus increasing patient's compliance.

Currently, colorectal cancer (CRC) screening rates remain suboptimal (~20%) and lag far behind those for breast, cervical and prostate cancer. Countries across the European Union have introduced CRC screening programs using colonoscopy, sigmoidoscopy, guaiac or immunochemical fecal occult blood testing (FOBT and FIT) for people aged over 50 years. Lack of compliance with screening recommendations is largely attributed to the unpleasant and cumbersome aspects of these methods. Therefore, it is imperative that a reliable, non-invasive, easy to use screening test is found to meet the needs of a large unscreened and aging population. A blood test would have the highest chance of acceptance by patients and by medical community.

The design and characteristics of the invention disclosed herein, in particular the use of blood and peripheral blood mononuclear cells (PBMCs) as testing specimen, establishes a new and more compliant screening method for pre-colonoscopy CRC testing.

Specifically, the present invention provides biomarkers related to colorectal tumors that, when used together in combinations of at least two core biomarkers with at least one high priority biomarker, which is individually selected from a panel of biomarker candidates, such biomarker combinations can be used to detect colorectal tumors. Accordingly, the present invention provides methods for screening, detecting, diagnosing and monitoring colorectal tumors by measuring the amount of each biomarker of at least three biomarkers of Table 1 in a sample (such as PBMCs or blood cells).

Particularly, the present invention provides a method that includes steps of (a) measuring in a sample obtained from a subject the amount of each biomarker of a biomarker panel including at least three biomarkers of Table 1; (b) calculating a probability score (or a probability value) based on the measurement of step (a); and (c-1) ruling out colorectal tumor for the subject if the score in step (b) is lower than a pre-determined score (or a pre-determined threshold) or (c-2) ruling in the likelihood of colorectal tumor for the subject if the score in step (b) is higher than a pre-determined score (or a pre-determined threshold).

In some embodiments, the method includes steps of (a) collecting a nucleic acid sample from a biological sample (e.g., peripheral blood mononuclear cells or blood cells) obtained from a subject; (b) measuring in the nucleic acid sample the amount of each biomarker of a biomarker panel including at least three biomarkers of Table 1; (c) calculating a probability score (or a probability value) based on the measurement of step (b); and (d-1) ruling out colorectal tumor for the subject if the score in step (c) is lower than a pre-determined score (or a pre-determined threshold) or (d-2) ruling in the likelihood of colorectal tumor for the subject if the score in step (c) is higher than a pre-determined score (or a pre-determined threshold).

For example, the at least three biomarkers of Table 1 include at least one high priority biomarker and at least two core biomarkers selected from the group consisting of IL1B, PTGS2, S100A8, LTF, CXCL10 and CACNB4. For example, the at least three biomarkers of Table 1 include IL1B, PTGS2 and S100A8.

When colorectal tumor is ruled out the subject does not receive a treatment protocol. However, when colorectal tumor is ruled in the subject receives a treatment protocol. The treatment protocol may include, but is not limited to, a colonoscopy, a biopsy, a surgery, a chemotherapy, a radiotherapy, or any combination thereof.

The probability score can be calculated according to any method known in the art. For example, the probability score is calculated from a logistic regression prediction model applied to the measurement. For example, the probability score is calculated by:

$$\log\left(\frac{Pr(y_i = 1)}{1 - Pr(y_i = 1)}\right) = \beta_0 + \beta_1 x_{1,i} + \ldots + \beta_m x_{m,i}$$

and where $x_{m,i}$ is a measured value for the biomarker m and subject i and $(\beta_0, \beta_1, \ldots, \beta_m)$ is a vector of coefficients. In other words, $\beta_0$ is a panel-specific constant, and $\beta_m$ is the corresponding logistic regression coefficient of the biomarker m.

In some embodiments, the likelihood of colorectal tumor is also determined by the sensitivity, specificity, negative predictive value (NPV) or positive predictive value (PPV) associated with the score.

The present invention also provides a method that includes steps of (a) measuring in a sample obtained from a subject the amount of each biomarker of a biomarker panel including at least three biomarkers of Table 1; (b) comparing the amount measured in step (a) to a reference value; and (c) classifying the subject as more likely to have colorectal tumor when an increase or a decrease in the amount of each biomarker of the biomarker panel relative to the reference value is detected in step (b).

In some embodiments, the method includes the steps of (a) collecting a nucleic acid sample from a biological sample (e.g., peripheral blood mononuclear cells or blood cells) obtained from a subject; (b) measuring in the nucleic acid sample the amount of each biomarker of a biomarker panel including at least three biomarkers of Table 1; (c) comparing the amount measured in step (b) to a reference value; and (d) classifying the subject as more likely to have colorectal tumor when an increase or a decrease in the amount of each biomarker of the biomarker panel relative to the reference value is detected in step (c).

For example, the at least three biomarkers of Table 1 include at least one high priority biomarker and at least two core biomarkers selected from the group consisting of IL1B, PTGS2, S100A8, LTF, CXCL10 and CACNB4. For example, the at least three biomarkers of Table 1 include IL1B, PTGS2 and S100A8.

In some embodiments, the method further includes a step of (i) selecting a treatment regimen (or protocol) for the subject classified as more likely to have colorectal tumor or (ii) administering to the subject classified as more likely to have colorectal tumor a therapeutically effective amount of at least one colorectal cancer-modulating agent.

Treatment regimen for colorectal cancer is standard of care for the treatment of colorectal tumor (e.g., colorectal polyps such as adenomas and colorectal carcinomas) as described in the most current National Comprehensive Cancer Network (NCCN) guidelines. The treatment regimen may include administering a therapeutically effective amount of at least one colorectal cancer-modulating agent.

The one or more colorectal cancer-modulating agents can comprise an alkylating agent, an antibiotic agent, an antimetabolic agent, a hormonal agent, a plant-derived agent, a retinoid agent, a tyrosine kinase inhibitor, a biologic agent, a gene therapy agent, a histone deacetylase inhibitor, other anti-cancer agent, or combinations thereof. Exemplary colorectal cancer-modulating agents include, but are not limited to, Adrucil (Fluorouracil), Avastin (Bevacizumab), Bevacizumab, Camptosar Orinotecan Hydrochloride), Capecitabine, Cetuximab, Efudex (Fluorouracil), Eloxatin (Oxaliplatin), Erbitux (Cetuximab), Fluoroplex (Fluorouracil), Fluorouracil, Irinotecan Hydrochloride, Leucovorin Calcium, Oxaliplatin, Panitumumab, Regorafenib, Stivarga (Regorafenib), Vectibix (Panitumumab), Wellcovorin (Leucovorin Calcium), Xeloda (Capecitabine), Zaltrap (Ziv-Aflibercept), and Ziv-Aflibercept.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, the improvements in colorectal cancer risk factors as a result of treatment with one or more colorectal cancer-modulating agents can comprise a reduction in polyp formation, a reduction in polyp size, a reduction in polyp number, a reduction in symptoms of ulcerative colitis, inflammatory bowel disease, and/or Crohn's disease, or combinations thereof.

The present invention also provides at least three biomarkers of Table 1 for use in a method of determining the likelihood of colorectal tumor, detecting colorectal tumor, diagnosing colorectal tumor and/or monitoring colorectal tumor. The method may include the steps of:

(I) (a) measuring in a nucleic acid sample from a biological sample (e.g., peripheral blood mononuclear cells or blood cells) the amount of each biomarker of the at least three biomarkers of Table 1; (b) calculating a probability score based on the measurement of step (a); and (c-1) ruling out colorectal tumor for the subject if the score in step (c) is lower than a pre-determined score (or a pre-determined threshold) or (c-2) ruling in the likelihood of colorectal tumor for the subject if the score in step (b) is higher than a pre-determined score (or a pre-determined threshold); or (II) (a) measuring in a nucleic acid sample from a biological sample (e.g., peripheral blood mononuclear cells or blood cells) the amount of each biomarker of the at least three biomarkers of Table 1; (b) comparing the amount measured in step (a) to a reference value; and (c) classifying the subject as more likely to have colorectal tumor when an increase or a decrease in the amount of each biomarker of the biomarker panel relative to the reference value is detected in step (b).

For example, the at least three biomarkers of Table 1 include at least one high priority biomarker and at least two core biomarkers selected from the group consisting of IL1B, PTGS2, S100A8, LTF, CXCL10 and CACNB4. For example, the at least three biomarkers of Table 1 include IL1B, PTGS2 and S100A8.

The measuring step of any method or use described herein may include a step of contacting the nucleic acid sample obtained from the subject with one or more primers described herein that specifically hybridize to the biomarker of interest. The measuring step may further include a step of amplifying the biomarker of interest with such one or more primers.

The actual measurement of levels of the biomarkers can be determined at the nucleic acid or protein level using any method known in the art. For example, at the nucleic acid level, the biomarkers can be measured by extracting ribonucleic acids from the sample and performing any type of quantitative PCR on the reverse-transcribed nucleic acids. Another way to detect the biomarkers can also be by a whole transcriptome analysis based on high-throughput sequencing methodologies, e.g., RNA-seq, or on microarray technology, e.g., Affymetrix arrays.

By way of example, other methods that can be used for measuring the biomarker may involve any other method of quantification known in the art of nucleic acids, such as but not limited to amplification of specific sequences, oligonucleotide probes, hybridization of target genes with complementary probes, fragmentation by restriction endonucleases and study of the resulting fragments (polymorphisms), pulsed field gels techniques, isothermic multiple-displacement amplification, rolling circle amplification or replication, immuno-PCR, among others known to those skilled in the art.

By using information provided by database entries for the biomarker sequences, biomarker expression levels can be detected and measured using techniques well known to one of ordinary skill in the art. For example, biomarker sequences within the sequence database entries, or within the sequences disclosed herein, can be used to construct probes and primers for detecting biomarker mRNA sequences in methods which specifically, and, preferably, quantitatively amplify specific nucleic acid sequences such as reverse-transcription based real-time polymerase chain reaction (RT-qPCR).

Levels of biomarkers can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Alternatively, a suitable method can be selected to determine the activity of proteins encoded by the biomarker genes according to the activity of each protein analyzed.

The biomarker proteins, polypeptides, mutations, and polymorphisms thereof can be detected in any suitable manner, but is typically detected by contacting a sample from the subject with an antibody which binds the biomarker protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample used to conduct the method described above.

Those skilled in the art will be familiar with numerous specific immunoassay and nucleic acid amplification assay formats and variations thereof which may be useful for carrying out the embodiments of the invention disclosed herein.

Preferably, expression levels of the biomarkers of the present invention are detected by RT-qPCR, and in particular by real-time PCR, as described further herein.

In general, total RNA can be isolated from the target sample, such as peripheral blood or PBMC, using any isolation procedure. This RNA can then be used to generate first strand copy DNA (cDNA) using any procedure, for example, using random primers, oligo-dT primers or random-oligo-dT primers which are oligo-dT primers coupled on the 3'-end to short stretches of specific sequence covering all possible combinations. The cDNA can then be used as a template in quantitative PCR.

In real-time PCR quantification of PCR products relies, for example, on increases in fluorescence, released at each amplification cycle of the reaction, for example, by a probe that hybridizes to a portion of the amplification product. Fluorescence approaches used in real-time quantitative PCR are typically based on a fluorescent reporter dye such as FAM, fluorescein, HEX, TET, etc. and a quencher such as TAMRA, DABSYL, Black Hole, etc. When the quencher is separated from the probe during the extension phase of PCR, the fluorescence of the reporter can be measured. Systems like Universal ProbeLibrary, Molecular Beacons, Taqman Probes, Scorpion Primers or Sunrise Primers and others use this approach to perform real-time quantitative PCR. Alternatively, fluorescence can be measured from DNA-intercalating fluorochromes such as Sybr Green.

The abundance of target RNA molecules can be performed by real-time PCR in a relative or absolute manner. Relative methods can be based on the threshold cycle determination (Ct) or, in the case of the Roche's PCR instruments, the crossing point (Cp). Relative RNA molecule abundance is then calculated by the delta Ct (delta Cp) method by subtracting Ct (Cp) value of one or more housekeeping genes. An example of housekeeping genes which can be used are reported in Table 2. Alternatively, absolute measurement can be performed by determining the copy number of the target RNA molecule by the mean of standard curves.

Table 1 lists an example of forward and reverse primers as well as the identification number of the Universal ProbeLibrary probe (Roche) which could be used for the measurement of the correspondent biomarker by real-time PCR.

The biomarkers and methods of the present invention allow one of skill in the art to screen, identify, diagnose, or otherwise assess those subjects who do not exhibit any symptoms of colorectal tumors, but who nonetheless may be at risk for developing colorectal tumors, or for experiencing symptoms characteristic of a cancerous condition.

Table 1 provides information including a non-exhaustive list of peripheral blood biomarkers related to colorectal tumors according to the invention. One skilled in the art will recognize that the biomarkers presented herein encompasses proteins, nucleic acids (cDNAs, mRNAs, RNAs, DNAs), and metabolites, together with their polymorphisms, mutants, isoform variants, related metabolites, derivatives, precursors including nucleic acids and pro-proteins, cleavage products, protein-ligand complexes, post-translationally modified variants (such as cross-linking or glycosylation), fragments, and degradation products, as well as any multi-unit nucleic acid, protein, and glycoprotein structures comprised of any of the biomarkers as constituent subunits of the fully assembled structure. All biomarkers expression within blood samples have been validated through experimentation.

TABLE 1

Blood biomarkers related to colorectal tumors

| Gene Symbol | Gene Description | Forward Primer Sequence (SEQ ID NO) | Reverse Primer Sequence (SEQ ID NO) | UPL Probe ID |
|---|---|---|---|---|
| BCL3 | B-cell CLL/lymphoma 3 | ACAACAACCTACGGC AGACA (1) | CCACAGACGGTAATGT GGTG (2) | 76 |
| CACNB4 | calcium channel, voltage-dependent, beta 4 subunit | TCCAAGCACAGCTAT CTCCTT (3) | CCCTCTTTCACCAGCC TTC (4) | 138 |
| CCR1 | chemokine (C-C motif) receptor 1 | AGTGATTTCCACAGT GACTCCA (5) | GGCAGATGCTGGCTAC TGAT (6) | 95 |
| CD63 | CD63 molecule | GAATGAAATGTGTGA AGTTCTTGC (7) | GCAATCAGTCCCACTG CAC (8) | 18 |

TABLE 1-continued

Blood biomarkers related to colorectal tumors

| Gene Symbol | Gene Description | Forward Primer Sequence (SEQ ID NO) | Reverse Primer Sequence (SEQ ID NO) | UPL Probe ID |
|---|---|---|---|---|
| CES1 | carboxylesterase 1 | CAGGAGTTTGGCTGG TTGAT (9) | CAGTTGCCCTTCGGAG AGT (10) | 136 |
| CXCL10 | chemokine (C-X-C motif) ligand 10 | AAAAGGTATGCAATC AAATCTGC (11) | AAGAATTTGGGCCCCT TG (12) | 86 |
| CXCL11 | chemokine (C-X-C motif) ligand 11 | TTGTGTGCTACAGTT GTTCAAGG (13) | TCTGCCACTTTCACTG CTTTA (14) | 81 |
| CXCR3 | chemokine (C-X-C motif) receptor 3 | ACCACAAGCACCAAA GCAG (15) | GGCGTCATTTAGCACT TGGT (16) | 27 |
| EGR1 | early growth response 1 | AGCACCTGACCGCAG AGT (17) | GGCAGTCGAGTGGTTT GG (18) | 54 |
| FXYD5 | FXYD domain containing ion transport regulator 5 | ACCACGTCCAGTTCT TCAGC (19) | GGGCTGGAGTTCTGTG TAGACT (20) | 45 |
| GATA2 | GATA binding protein 2 | CACAAGATGAATGGG CAGAA (21) | TGACAATTTGCACAAC AGGTG (22) | 117 |
| IL1B | interleukin 1, beta | AGCTGATGGCCCTAA ACAGA (23) | TCGGAGATTCGTAGCT GGAT (24) | 85 |
| IL8 | interleukin 8 | TAGCCAGGATCCACA AGTCC (25) | CTGTGAGGTAAGATGG TGGCTA (26) | 98 |
| ITGA2 | integrin, alpha 2 (CD49B) | AACATGAGCCTCGGC TTG (27) | GCCCACAGAGGACCAC AT (28) | 154 |
| ITGB5 | integrin, beta 5 | GCATGCAGCACCAAG AGAG (29) | GCAGGTCTGGTTGTCA GGTT (30) | 40 |
| JUN | jun proto-oncogene | AGTCAGGCAGACAGA CAGACAC (31) | AAAATAAGATTTGCAG TTCGGACTAT (32) | 20 |
| LTF | lactotransferrin | TAAGGTGGAACGCCT GAAAC (33) | CCATTTCTCCCAAATT TAGCC (34) | 22 |
| MAP2K3 | mitogen-activated protein kinase kinase 3 | CGAGTTTGTGGACTT CACTGC (35) | AAGGTGAAGAAGGGGT GCTC (36) | 1 |
| MAPK6 | mitogen-activated protein kinase 6 | TGGATGAAACTCACA GTCACATT (37) | GGCCAATCATGCTCTG AAA (38) | 48 |
| MMP11 | matrix metallopeptidase 11 (stromelysin 3) | AAGAGGTTCGTGCTT TCTGG (39) | CCATGGGAACCGAAGG AT (40) | 14 |
| MMP9 | matrix metallopeptidase 9 (gelatinase B) | ATCCGGCACCTCTAT GGTC (41) | CAGACCGTCGGGGAG (42) | 77 |
| MSL1 | male-specific lethal 1 homolog (Drosophila) | CAGGCCAAGGAAAAG GAGAT (43) | CGTTCAATCCGAGCAA GG (44) | 17 |
| NME1 | non-metastatic cells 1, protein (NM23A) | CCTAAGCAGCTGGAA GGAAC (45) | CGCTTGATAATCTCTC CCACA (46) | 100 |
| PPARG | peroxisome proliferator-activated receptor gamma | GACAGGAAAGACAAC AGACAAATC (47) | GGGGTGATGTGTTTGA ACTTG (48) | 7 |
| PTGES | prostaglandin E synthase | AGAAGGCCTTTGCCA ACC (49) | GATGGTCTCCATGTCG TTCC (50) | 122 |
| PTGS2 | prostaglandin-endoperoxide synthase 2 | CGCTCAGCCATACAG CAA (51) | TCATACATACACCTCG GTTTTGA (52) | 150 |
| RHOC | ras homolog gene family, member C | AGCACACCAGGAGAG AGCTG (53) | GTAGCCAAAGGCACTG ATCC (54) | 92 |

TABLE 1-continued

Blood biomarkers related to colorectal tumors

| Gene Symbol | Gene Description | Forward Primer Sequence (SEQ ID NO) | Reverse Primer Sequence (SEQ ID NO) | UPL Probe ID |
|---|---|---|---|---|
| S100A8 | S100 calcium binding protein A8 | CAGCTGTCTTTCAGA AGACCTG (55) | CTTTCTCCAGCTCGGT CAAC (56) | 105 |
| TNFSF13B | tumor necrosis factor (ligand) superfamily, member 13b | CTCAAGACTGCTTGC AACTGA (57) | AAGCTGAGAAGCCATG GAAC (58) | 112 |

TABLE 2

Housekeeping genes used for gene expression normalization

| Gene Symbol | Gene Description | Forward Primer Sequence (SEQ ID NO) | Reverse Primer Sequence (SEQ ID NO) | UPL Probe ID |
|---|---|---|---|---|
| NACA | nascent polypeptide-associated complex alpha subunit | TGCTACAGAGCAGG AGTTGC (59) | TCCTGTTCTTCAAGCT CTGGT (60) | 45 |
| RPLP0 | ribosomal protein, large, P0 | TCGACAATGGCAGC ATCTAC (61) | GCCAATCTGCAGACAG ACAC (62) | 6 |
| TPT1 | tumor protein, translationally-controlled 1 | CAATCAAAGGGAAA CTTGAAGAA (63) | GATTCATGTTTTCACC AATAAAGAAC (64) | 54 |

These blood biomarkers can be measured and used in combination in a prediction model that comprises three or more biomarkers. In some aspects, all 29 biomarkers listed in Table 1 can be measured and used. Preferred ranges from which the number of biomarkers are measured and used include ranges bounded by any minimum selected from between 3 and 29.

In certain embodiments, the at least three biomarkers of Table 1 include (a) IL1B, PTGS2, LTF; (b) IL1B, PTGS2, S100A8; (c) IL1B, PTGS2, S100A8, LTF; or (d) IL1B, PTGS2, S100A8, LTF.

In particular, the at least three biomarkers of Table 1 include at least two core biomarkers (also called indispensable biomarkers) in combination with at least one high priority biomarker, which is individually selected from a panel of biomarkers.

A "core biomarker" used herein refers to a biomarker that has a level of importance of 1 or 2, according to Table 6. A core biomarker is selected from the group consisting of IL1B, PTGS2, S100A8, LTF, CXCL10 and CACNB4.

A "high priority biomarker" used herein refers to a biomarker that has a level of importance of 2, 3 or 4, according to Table 6.

In some embodiments, the at least three biomarkers of Table 1 utilized in any method or use described herein include at least one high priority biomarker and at least two core biomarkers selected from the group consisting of IL1B, PTGS2, S100A8, LTF, CXCL10 and CACNB4.

For example, the at least two core biomarkers are (a) IL1B and PTGS2; (b) IL1B, PTGS2 and S100A8; (c) IL1B, PTGS2, S100A8 and LTF; (d) IL1B, PTGS2, S100A8, LTF, and CXCL10; or (e) IL1B, PTGS2, S100A8, LTF, CXCL10 and CACNB4.

For example, the two core biomarkers are IL1B and PTGS2 and they are combined with at least one biomarker selected from the panel of high priority biomarkers that comprises S100A8, LTF, CXCL10, CACNB4, MMP9, CXCL11, EGR1, JUN, TNFSF13B, GATA2, MMP11, NME1, PTGES, CCR1, CXCR3, FXYD5, IL8, ITGA2, ITGB5, MAPK6, RHOC, BCL3, CD63, CES1, MAP2K3, MSL1 and PPARG.

Particularly, the panel of high priority biomarkers comprises S100A8, LTF, CXCL10, and/or CACNB4.

In any method and use described herein, 1, 2, 3, 4 or more high priority biomarkers can be utilized. For example, the at least one (1, 2, 3, 4, or more) high priority biomarker is selected from the group consisting of S100A8, LTF, CXCL10, CACNB4, MMP9, CXCL11, EGR1, JUN, TNFSF13B, GATA2, MMP11, NME1, PTGES, CCR1, CXCR3, FXYD5, IL8, ITGA2, ITGB5, MAPK6, RHOC, BCL3, CD63, CES1, MAP2K3, MSL1, and PPARG.

For example, the at least one high priority biomarker includes two biomarkers selected from the group consisting of S100A8, LTF, CXCL10 and CACNB4. For example, the at least one high priority biomarker includes three biomarkers selected from the group consisting of S100A8, LTF, CXCL10 and CACNB4. For example, the at least one high priority biomarker includes four biomarkers S100A8, LTF, CXCL10, and CACNB4.

For example, the high priority biomarkers are (a) CXCL10 and S100A8, (b) CXCL10 and LTF, (c) CXCL10 and CACNB4, (d) S100A8 and LTF, (e) S100A8 and CACNB4, (f) LTF and CACNB4, (g) CXCL10 and S100A8 and LTF, (h) CXCL10 and S100A8 and CACNB4, (i) CXCL10 and LTF and CACNB4, (j) S100A8 and LTF and CACNB4, or (k) CXCL10 and S100A8 and LTF and CACNB4.

In certain embodiments, the biomarkers used herein are any combinations of one combination from Group A with one combination from Group B, removing the duplicate if there is any (see Table below). For example, the biomarkers are combination (a) from Group A and combination (a) from Group B.

| Combinations of core biomarkers (Group A) | Combinations of high priority biomarkers (Group B) |
|---|---|
| (a) IL1B and PTGS2 | (a) CXCL10 and S100A8 |
| (b) IL1B, PTGS2 and S100A8 | (b) CXCL10 and LTF |
| (c) IL1B, PTGS2, S100A8 and LTF | (c) CXCL10 and CACNB4 |
| (d) IL1B, PTGS2, S100A8, LTF, and CXCL10 | (d) S100A8 and LTF |
| (e) IL1B, PTGS2, S100A8, LTF, CXCL10 and CACNB4 | (e) S100A8 and CACNB4 |
|  | (f) LTF and CACNB4 |
|  | (g) CXCL10, S100A8 and LTF |
|  | (h) CXCL10, S100A8 and CACNB4 |
|  | (i) CXCL10, LTF and CACNB4 |
|  | (j) S100A8, LTF and CACNB4 |
|  | (k) CXCL10, S100A8, LTF and CACNB4 |

In some embodiments, the core biomarkers are IL1B, PTGS2 and S100A8 and the high priority biomarkers are (i) BCL3, CACNB4, CCR1, CXCL10, ITGA2, ITGB5, LTF, MAP2K3, MAPK6, MMP11, PTGES, and TNFSF13B; or (ii) CACNB4, CXCL10, LTF, MMP11, and PTGES.

A "biomarker" used herein refers to a molecular indicator of a specific biological property; a biochemical feature or facet that can be used to detect colorectal cancer. "Biomarker" encompasses, without limitation, proteins, nucleic acids, and metabolites, together with their polymorphisms, mutants, isoform variants, related metabolites, derivatives, precursors including nucleic acids and pro-proteins, cleavage products, protein-ligand complexes, post-translationally modified variants (such as cross-linking or glycosylation), fragments, and degradation products, as well as any multi-unit nucleic acid, protein, and glycoprotein structures comprised of any of the biomarkers as constituent subunits of the fully assembled structure, and other analytes or sample-derived measures.

"Measuring", "measurement", "detection" and "detecting" mean assessing the presence, absence, quantity or amount (which can be an effective amount) of either a given substance within a clinical or subject-derived sample, including qualitative or quantitative concentration levels of such substances, or otherwise evaluating the values or categorization of a subject's clinical parameters.

"Altered", "an increase" or "a decrease" refers to a detectable change or difference between the measured biomarker and the reference value from a reasonably comparable state, profile, measurement, or the like. One skilled in the art should be able to determine a reasonable measurable change. Such changes may be all or none. They may be incremental and need not to be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold, 2-fold, 3-fold, 4-fold, 5-fold or more, or any values in between 1-fold and five-fold. The change may be statistically significant with a p value of 0.1, 0.05, 0.001, or 0.0001.

The term "colorectal tumor" is meant to include a broad spectrum of epithelial-derived tumors ranging from benign growths to invasive cancer. These include colorectal polyps, such as adenomas, and colorectal carcinomas.

The terms "adenomatous polyps", "adenoma" are used interchangeably.

The terms "individual", "host", "patient", and "subject" are used interchangeably. As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female.

A subject can be one who has not been previously diagnosed or identified as having colorectal tumor. A subject can be a healthy subject who is classified as low risk for developing a colon condition (such as colorectal polyps or colorectal cancer). Alternatively, a subject can be one who has a risk of developing colorectal tumor. A risk factor is anything that affects the subject's chance of getting a disease such as colorectal tumor. Risk factors that may increase a person's chance of developing colorectal polyps or colorectal cancer include, but are not limited to, age, history of colorectal polyps or colorectal cancer (especially true if the polyps are large or if there are many of them), history of inflammatory bowel disease (such as ulcerative colitis and Crohn's disease), history of colorectal cancer or adenomatous polyps, inherited genetic syndromes (such as familial adenomatous polyposis (FAP), hereditary non-polyposis colon cancer (HNPCC), Turcot syndrome, Peuz-Jegher syndrome, MUTYH-associated polyposis), type—diabetes, lifestyle related factors (diet, weight, and exercise), physical inactivity, obesity, smoking and heavy alcohol use.

A "sample" in the context of the present invention is a biological sample isolated from a subject and can include, by way of example and not limitation, whole blood, serum, plasma, blood cells, peripheral blood mononuclear cells, endothelial cells, circulating tumor cells, tissue biopsies, lymphatic fluid, ascites fluid, interstitial fluid, bone marrow, cerebrospinal fluid (CSF), saliva, mucous, sputum, sweat, urine, or any other secretion, excretion, or other bodily fluids. In some embodiments, the sample refers to peripheral blood mononuclear cells or blood cells.

"Peripheral blood mononuclear cell" (PBMC) refers to any cell present in the blood having a round nucleus. This fraction is conventionally isolated by centrifuging whole blood in a liquid density gradient. It contains mainly lymphocytes and monocytes while excluding red blood cells and granulocytes (eosinophils, basophils, and neutrophils). Rare cells with a round nucleus such as progenitor endothelial cells or circulating tumor cells could also be present in this fraction.

The term "primer" refers to a strand of nucleic acid that serves as a starting point for DNA replication.

The terms "probe" and "hydrolysis probe" refer to a short strand of nucleic acid designed to hybridize to a region within the amplicon and is dual labeled with a reporter dye and a quenching dye. The close proximity of the quencher suppresses the fluorescence of the reporter dye. The probe relies on the 5'-3' exonuclease activity of Taq polymerase, which degrades a hybridized non-extendible DNA probe during the extension step of the PCR. Once the Taq polymerase has degraded the probe, the fluorescence of the reporter increases at a rate that is proportional to the amount of template present.

The term "gene expression" means the production of a protein or a functional mRNA from its gene.

The terms "signature", "classifier", "model" and "predictor" are used interchangeably. They refer to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of nucleic acids or proteins in a biological sample. Protein or nucleic acid expression levels in a subject can be compared to levels in patients previously diagnosed as disease free or with a specified condition.

A "reference or baseline level/value" as used herein can be used interchangeably and is meant to be relative to a number or value derived from population studies, including without limitation, such subjects having similar age range, disease status (e.g., stage), subjects in the same or similar ethnic group, or relative to the starting sample of a subject undergoing treatment for cancer. Such reference values can be derived from statistical analyses and/or risk prediction data of populations obtained from mathematical algorithms and computed indices of colorectal cancer. Reference indices can also be constructed and used utilizing algorithms and other methods of statistical and structural classification.

In some embodiments of the present invention, the reference or baseline value is the expression level of a particular biomarker of interest in a control sample derived from one or more healthy subjects or subjects who have not been diagnosed with any cancer.

In some embodiments of the present invention, the reference or baseline value is the expression level of a particular biomarker of interest in a sample obtained from the same subject prior to any cancer treatment. In other embodiments of the present invention, the reference or baseline value is the expression level of a particular biomarker of interest in a sample obtained from the same subject during a cancer treatment. Alternatively, the reference or baseline value is a prior measurement of the expression level of a particular gene of interest in a previously obtained sample from the same subject or from a subject having similar age range, disease status (e.g., stage) to the tested subject.

The term "ruling out" as used herein is meant that the subject is selected not to receive a treatment protocol.

The term "ruling in" as used herein is meant that the subject is selected to receive a treatment protocol.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein (nucleic acid), the absolute value for the expression of the protein (nucleic acid) can be expressed in terms of an absolute value for the expression of a standard protein (nucleic acid) that is substantially constant in expression. This prevents the technical variation of sample preparation and PCR measurement from impeding the measurement of protein (nucleic acid) concentration levels in the sample.

The term "score" or "scoring" refers to calculating a probability likelihood (or a probability value) by the model (e.g., a logistic regression model) for a sample. For the present invention, values closer to 1.0 are used to represent the likelihood that a sample is derived from a patient with a colon condition (such as an polyps, adenoma, colorectal carcinomas, or colorectal tumors), values closer to 0.0 represent the likelihood that a sample is derived from a patient without a colon condition (such as an polyps, adenoma, colorectal carcinomas, or colorectal tumors).

A "pre-determined score" refers to a probability threshold that has been determined during the modeling/training phase by, for instance, logistic regression and ROC analysis, and that defines the likelihood of colorectal tumor and/or diagnosis of colorectal tumor. A skilled artisan can readily determine such score according to any methods available in the art.

The proposed method for analyzing and using a biomarker profile for detection, diagnosis and monitoring of colorectal tumors is to a) extract RNA from peripheral blood mononuclear cells, b) reverse-transcribe said RNA into cDNA, c) perform a real-time PCR amplification specific for each biomarker of interest and d) perform statistical data analysis derived from disclosed composition and methods, using, for example, penalized logistic regression to build prediction models.

By way of example and not intended to limit any aspect of the present invention, other compositions and methods can be applied for analyzing data derived from the measurement of one or more biomarkers of the present invention.

All data and statistical analyses can be conducted on R software (R-CRAN free software environment for statistical computing and graphics), MATLAB (The MathWorks), SPSS (IBM), SYSTAT (Systat Software Inc.), and other supports allowing numerical analyses.

Methods that can be used for analyzing data derived from the measurement of said biomarkers related to colorectal tumors involves any art-recognized statistical analysis of data, such as logistic and penalized logistic regression, support vector machine, random forest, fuzzy logic, neural network, gene clustering, data mining tools, and other algorithms or computed indices known in the art and disclosed herein.

Logistic regression (McCullagh, P. and Nelder, A. (1983) *Generalized linear models, Monographs on Statistics and Applied Probability*) is one of the common methods to discriminate two groups. If we define $y_i$ as being 0 or 1 according to its group, we can model through a logistic regression as $$\log\left(\frac{Pr(y_i = 1)}{1 - Pr(y_i = 1)}\right) = \beta_0 + \beta_1 x_{1,i} + \ldots + \beta_m x_{m,i}$$

Where $x_{m,i}$ is a deltaCp value for the biomarker m and subject i and $(\beta_0, \beta_1, \ldots, \beta_m)$ is a vector of coefficients (parameters to be estimated) for a multivariate logistic regression. To estimate these parameters one can use the maximum likelihood method.

For example, adenoma can be determined by a predictive model equation:

$$\log\left(\frac{Pr(y_i = 1)}{1 - Pr(y_i = 1)}\right) = -0.668 + 0.07 \times BCL3 + 0.449 \times CACNB4 -$$
$$0.274 \times CCR1 + 0.174 \times CXCL10 - 0.260 \times IL1B - 0.115 \times ITGA2 -$$
$$0.083 \times ITGB5 - 0.130 \times LTF - 0.024 \times MAP2K3 -$$
$$0.213 \times MAPK6 + 0.297 \times MMP11 + 0.001 \times PTGES -$$
$$0.140 \times PTGS2 - 0.145 \times S100A8 - 0.212 \times TNFSF13B.$$

For example, carcinoma can be determined by a predictive model equation:

$$\log\left(\frac{Pr(y_i = 1)}{1 - Pr(y_i = 1)}\right) = -8.544 + 0.707 \times CACNB4 +$$
$$0.688 \times CXCL10 - 0.592 \times IL1B - 0.234 \times LTF + 0.044 \times MMP11 +$$
$$0.105 \times PTGES - 0.143 \times PTGS2 - 1.605 \times S100A8.$$

It is noted that for high dimensional data set with multi-co-linearity, the logistic regression can fail. Since some of the selected biomarkers might be highly correlated, a solution is to use penalized logistic regression.

Penalized logistic regression is based on mathematical equation derived from logistic regression. More specifically, penalized logistic regression is a ridge regression for logistic model with L2-norm or L1-norm penalty. To estimate the parameters in this method a quadratic (L2) or/and L1-norm penalty is added on the log-likelihood that should be maximized. To choose the best value of $\lambda_1$ and $\lambda_2$, the cross-validation is used with the A1C criteria. To fit the penalized logistic model, the following algorithms (packages in R Cran, statistical software) can be used: glmpath (Park M. Y and Hastie T. (2006) *An L1 Regularization-path Algorithm for Generalized Linear Models. A generalization of the LARS algorithm for GLMs and the Cox proportional hazard model*), penalized (Goeman, J. (2010) *L1 (lasso) and L2 (ridge) penalized estimation in GLMs and in the Cox model*) and glmnet (Hasti, T., Tibshirani and R., Friedman, J. (2010). *Lasso and elastic-net regularized generalized linear models*) with different tuning parameters.

The application of logistic regression to biological problems is routine in the art. Various statistical analysis softwares, such as the ones mentioned above, can be used for building logistic regression models. Fitted logistic regression models are tested by asking whether the model can correctly predict the clinical outcome using patient data other than that with which the logistic regression model was fitted, but having a known clinical outcome. After training, the model output from 0 (control) to 1 (cancer) can be calculated in blind fashion by the average error of all N predictions (a validation group). Based on the output values, the receiver operating characteristic (ROC) curve can be built to calculate the outcome of clinical prediction: specificity and sensitivity of CRC cancer detection. They are statistical measures of the performance of a binary classification test. Sensitivity measures the proportion of actual positives which are correctly identified as such (e.g., the percentage of sick people who are correctly identified as having the condition). Specificity measures the proportion of negatives which are correctly identified (e.g., the percentage of healthy people who are correctly identified as not having the condition). A perfect predictor would be described as 100% sensitive (i.e., predicting all people from the sick group as sick) and 100% specific (i.e., not predicting anyone from the healthy group as sick). However, any predictor will possess a minimum error bound.

One embodiment of the present invention is a predictive model comprising a combination/profile of peripheral blood mononuclear cell biomarkers detecting colorectal tumors preferably with sensitivity equal or above to 60% and specificity equal or above 84%.

The term "sensitivity of a test" refers to the probability that a test result will be positive when the disease is present in the patient (true positive rate). This is derived from the number of patients with the disease who have a positive test result (true positive) divided by the total number of patients with the disease, including those with true positive results and those patients with the disease who haven negative result, i.e., false negative.

The term "specificity of a test" refers to the probability that a test result will be negative when the disease is not present in the patient (true negative rate). This is derived from the number of patients without the disease who have a negative test result (true negative) divided by all patients without the disease, including those with a true negative result and those patients without the disease who have a positive test result, e.g. false positive. While the sensitivity, specificity, true or false positive rate, and true or false negative rate of a test provide an indication of a test's performance, e.g. relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" refers to the probability that a negative test correctly identifies a patient without the disease, which is the number of true negatives divided by the sum of true negatives and false negatives. Like the PPV, it also is inherently impacted by the prevalence of the disease and pre-test probability of the population intended to be tested. A positive result from a test with a sufficient PPV can be used to rule in the disease for a patient, while a negative result from a test with a sufficient NPV can be used to rule out the disease, if the disease prevalence for the given population, of which the patient can be considered apart, is known.

A "Receiver Operating Characteristics (ROC) curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.8, 0.9 to 0.95, or 0.95 to 1.0.

The methods provided herein are minimally invasive and pose little or no risk of adverse effects. As such, they may be used to diagnose, monitor and provide clinical management of subjects who do not exhibit any symptoms of a colon condition (colorectal tumor) and subjects classified as low risk for developing a colon condition (colorectal tumor). For example, the methods disclosed herein may be used to diagnose colorectal tumor in a subject who does not present with a colorectal polyp and/or has not presented with a colorectal polyp in the past, but who nonetheless deemed at risk of developing a colorectal polyp and/or a colon condition. Similarly, the methods disclosed herein may be used as a strictly precautionary measure to diagnose healthy subjects who are classified as low risk for developing a colon condition.

The invention further provides a kit to be used according to the aforementioned method for detecting the presence of colorectal tumors from a peripheral blood sample, in particular from a sample of peripheral blood mononuclear cells (PBMC). The kit may comprise one or more than one primer pair for measuring one or more biomarkers listed in Table 1, particularly the panel of biomarkers as described herein. Moreover, the kit may comprise primer pairs specific for one or more housekeeping genes, for example for the genes TPT1, RPLP0 and NACA described in Table 2. The kit may further comprise one or more probes, reference samples for performing measurement quality controls, plastic containers and reagents for performing test reactions and instructions for using the reagents in the method of any one of the preceding claims. Optionally, a kit may comprise instructions for use in the form of a label or a separate insert. The kits can contain reagents that specifically bind to proteins in the panels described, herein. These reagents can include antibodies.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the present disclosure.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLE

Methods for Colorectal Cancer Detection from a Blood Sample
Patients and Samples 181 subjects older than 50 years were prospectively enrolled in a case-control study including six centres. Upon colonoscopy, they were diagnosed to be control subjects (n=75), patients with adenoma≥1 cm (n=61) or patients with colorectal cancer (CRC) stage I-IV (n=45). Written informed consent was obtained from all study participants adhering to the local ethical guidelines. All subjects had no first-degree family history of CRC or a known CRC predisposition, previous history of cancer, no autoimmune or other inflammatory disorders, fever (>38° C.) or infections within the last 4 weeks before colonoscopy, nor any other disease defined in the study. Blood from all subjects has been drawn either up to 30 days before or up to 12 weeks after colonoscopy and prior to any polyp resection or any cancer specific treatment. Adenoma and cancer diagnosis was confirmed histologically from biopsy or surgical specimen.

Blood Collection and RNA Extraction

All enrolled subjects had a blood sample drawn. Peripheral blood samples for Colox® test were collected into Becton Dickinson (BD) Vacutainer® CPT™ tubes (4×4 ml). Filled CPT™ tubes were kept at room temperature and blood mononuclear cells (PBMC) separation performed within 6 hours according to manufacturer's instructions. PBMC pellets were resuspended in RNAlater® Solution (Life Technologies) and stored at −20° C.

Automated purification of total RNA was performed on QIAcube by RNeasy Mini kit (QIAGEN). This included an DNase treatment. RNA concentration was measured by Nanodrop spectrophotometer and RNA quality control was performed by Agilent 2100 Bioanalyzer (Agilent Technologies). Samples with a RIN<5 were considered of poor quality and discarded. Isolated total RNA was aliquoted and stored at −80° C.

Primers and Probes

Real-time PCR assays were purchased from Roche (Real-Time ready Custom RT-qPCR Assays) and were based on short hydrolysis Universal ProbeLibrary (UPL) probes. UPL is based on only 165 short hydrolysis probes (8-9 nucleotides). They are labeled at the 5' end with fluorescein (FAM) and at the 3' end with a dark quencher dye. In order to maintain the specificity and melting temperature (Tm) that hybridizing qPCR probes require, Locked Nucleic Acids (LNA) are incorporated into the sequence of each UPL probe. LNA's are DNA nucleotide analogues with increased binding strengths compared to standard DNA nucleotides.

Forward and reverse primer sequences as well as the UPL probe identification number are listed in table 1. Real-time PCR assays were pre-loaded on RealTime Ready™ Custom panel 384-32, 384-wells LC480 plates (Roche).

Quantitative RT-PCR 200 ng of total RNA was reverse transcribed into cDNA using SuperScript® VILO cDNA Synthesis Kit (Invitrogen) according to manufacturer's instructions.

Real-time PCR analysis was performed on the Lightcycler 480 instrument. PCR reactions were carried out in duplicates in 384-well plate in 10 μl of total volume. Each well was loaded with 5 μl of RealTime Ready™ DNA Probes Master Mix (Roche) and the cDNA equivalent of 2.5 ng of total RNA by MICROLAB® STARLet pipetting robot (Hamilton). Amplification was performed after 1 minute at 95° C. for the Taq DNA Polymerase activation which was followed by 40 cycles of 2 sec at 95° C. and 30 sec at 60° C. Positive and negative control samples were generated with each RT batch and were included in each plate and for each assay. The negative control was a RT-PCR mixture without RNA and cDNA to confirm no contamination occurred during the assay. The positive control was made with a standardised quantity of Human Universal Reference RNA (Clontech) aliquoted and stored at −80° C. For PCR run validation, the negative control should yield no amplification or a Crossing point (Cp) (the Lightcycler analogue of Ct) value up or equal to 35, and the positive control a Cp value, for each target gene, that falls within a pre-determined range. Cp values are automatically calculated by the Abs Quant/2nd Derivative Max method of the LightCycler 480 analysis software. Gene expression values (Cp) were normalized by the delta Ct method according to the formula: deltaCp=$Cp_{target}$−$Cp_{ref}$. In our case the $Cp_{ref}$ is the mean Cp value of 3 reference genes (RPLP0, NACA, TPT1).

Statistical Analysis

Normalized gene expression values (deltaCp) were used for all statistical analyses, which were performed with R software (R-CRAN free software environment for statistical computing and graphics). All the laboratory analyses were performed in a blind fashion. Once the samples were medically reviewed and the data locked according to the Diagnoplex Data Management Manual, the trial statistician became un-blinded for the analysis.

biomarkers has been compared across samples and expression levels were in general homogeneous.

Analysis of quintile distribution in each biomarker was performed through quintile-quintile plot (Q-Q plot) against a theoretical normal distribution. In general, biomarker expression values were normally distributed and only few biomarkers show a deviation from the reference distribution in the tails. Correlation analysis (Pearson's) and hierarchical clustering of 29 biomarkers have been performed. Only few variables appeared to be strongly correlated (CXCL10 and CXCL11, IL1B and PTGS2, EGR1 and PTGS2: correlation coefficient: 0.8; S110A8 and TNFSF13B, ITGB5 and ITGA2, JUN and IL8 correlation coefficient: 0.7); the remaining genes show only weak or no correlation.

TABLE 4

Study cohort demographic characteristics

|  | Controls | Adenoma ≥ 1 cm | CRC | StageI | StageII | StageIII | StageIV | Stage Unknown |
|---|---|---|---|---|---|---|---|---|
| Total No. | 124 | 100 | 74 | 20 | 15 | 21 | 18 | 8 |
| Age (mean ± S.D.) | 60.7 ± 7.7 | 67.4 ± 8.1 | 69.5 ± 9.8 | 70.7 ± 9.1 | 70.3 ± 8.06 | 68.0 ± 12.5 | 69.3 ± 7.3 | 70.4 ± 11.1 |
| Male (%) | 45% | 64% | 62.2% | 65% | 60% | 57.1% | 66.6% | 87.5% |
| Female (%) | 55% | 36% | 37.8% | 35% | 40% | 42.9% | 34.4% | 12.5% |

181 subjects were grouped according to diagnosis, gender and country of origin and were randomly assigned to a training and validation set, with the proportion of two third (n=120) and one third (n=61), respectively. Sample distribution across the three groups under investigation is reported in Table 3. This sample size allowed a significance level $\alpha$=0.05 and a power 1−$\beta$=0.90.

TABLE 3

Sample distribution in the control, adenoma and carcinoma groups of Training and Validation set.

|  |  | Training Set | Validation set |
|---|---|---|---|
| Controls |  | 50 | 25 |
| Adenoma ≥1 cm |  | 40 | 21 |
|  | Adenoma 1 cm-2 cm | 24 | 10 |
|  | Adenoma ≥2 cm | 16 | 11 |
| CRC |  | 30 | 15 |
|  | StageI | 9 | 3 |
|  | StageII | 4 | 5 |
|  | StageIII | 10 | 3 |
|  | StageIV | 7 | 4 |

Subjects in the training set were used to fit penalized logistic regression models regarding to the hypothesis control versus CRC and control versus adenoma≥1 cm. The prediction error for the fitted models was estimated on validation set. Predictive classifiers were selected according to the performances on training and validation set. Training and validation set predictions were used to determine the performances of the test such as specificity (true negative/total control) and sensitivity (true positive/total disease) for CRC and adenoma≥1 cm detection.

Results

Descriptive Analysis

Age, gender, sample collection site had no influence on gene expression analysis. Normalized gene expression of 29

Biomarker Analysis and Ranking

The dataset underwent a series of statistical tests to determine the statistical significance of each of the 29 biomarkers in discriminating controls from carcinoma or adenoma samples. By drawing with replacement from the training set (bootstrap method), sets of samples of equal size as the original set were created. This was repeated independently 1000 times. Student's t-test, univariate logistic regression (Dobson, A. J. (2002) *An introduction to generalized linear models, 2nd ed., Chapman & Hall/CRC Texts in Statistical Science Series*, McCullagh, P. and Nelder, J. A. (1983) *Generalized linear models, Monographs on Statistics and Applied Probability*), and Wilcoxon rank test were applied to the training set (Table 5) and to each of the bootstrap-derived sets. Moreover, gene expression fold-change (FC) between control and CRC or large adenomas was calculated for each biomarker in the 1000 sets. The results obtained were summarized for each biomarker by the frequency of significant p-values (<0.01 or 0.05) out of 1000 results and by the mean gene expression fold-change. All test results were categorized by magnitude and a partial score given to each category. A final score was obtained by the sum of partial scores resulting the ranking of the 29 biomarkers (Table 5).

Based on the score obtained, six biomarkers, IL1B, CCR1, PTGS2, S100A8, PPARG and, LTF appeared to be very strong in discriminating control from carcinoma samples by univariate analysis. All those genes were upregulated in PBMC from cancer patients. The best three down-regulated genes were: CACNB4, MMP11 and CXCL10.

TABLE 5

The biomarkers were ranked according to their ability to separate the control subjects from the CRC group. This ability is summarized by a score derived from a series of statistical analysis described above. As example, t-test p-value and gene expression fold-change (FC) are listed.

| | Biological Function | Wilcoxon p-value | Freq. p-value <0.01/1000 | FC CRC/Con | Direction |
|---|---|---|---|---|---|
| IL1B | Immune Response/Inflammation/Chemotaxis | 4.19E−04 | 847 | 2.14 | Up |
| CCR1 | Cell adhesion/Chemotaxis | 4.42E−04 | 860 | 1.65 | Up |
| PTGS2 | Lipid metabolism | 7.68E−04 | 804 | 2.11 | Up |
| S100A8 | Immune Response/Inflammation/Chemotaxis | 5.07E−06 | 992 | 1.65 | Up |
| PPARG | Transcription/Cell cycle/Regulation | 3.59E−03 | 656 | 1.41 | Up |
| LTF | Ion transport | 2.14E−02 | 419 | 2.36 | Up |
| EGR1 | Transcription/Cell cycle/Regulation | 3.79E−01 | 64 | 1.42 | Up |
| MAPK6 | Transcription/Cell cycle/Regulation | 3.95E−03 | 661 | 1.15 | Up |
| CACNB4 | Ion transport | 1.31E−02 | 452 | 1.30 | Down |
| MMP11 | Collagen degradation | 1.66E−02 | 442 | 1.30 | Down |
| TNFSF13B | Immune Response/Inflammation/Chemotaxis | 1.03E−02 | 524 | 1.21 | Up |
| CXCL10 | Immune Response/Inflammation/Chemotaxis | 7.13E−02 | 220 | 1.29 | Down |
| CD63 | Differentiation/Structure | 3.14E−02 | 375 | 1.14 | Up |
| CES1 | Immune Response/Inflammation/Chemotaxis | 5.70E−02 | 263 | 1.18 | Up |
| MMP9 | Collagen degradation | 1.21E−01 | 140 | 1.35 | Up |
| PTGES | Lipid metabolism | 3.28E−01 | 47 | 1.27 | Down |
| BCL3 | Transcription/Cell cycle/Regulation | 1.67E−01 | 110 | 1.12 | Up |
| CXCR3 | Immune Response/Inflammation/Chemotaxis | 8.04E−01 | 14 | 1.04 | Down |
| FXYD5 | Cell adhesion/Chemotaxis | 9.48E−01 | 7 | 1.00 | Up |
| GATA2 | Transcription/Cell cycle/Regulation | 6.40E−01 | 16 | 1.09 | Down |
| IL8 | Transcription/Cell cycle/Regulation | 9.76E−01 | 18 | 1.04 | Up |
| ITGA2 | Transcription/Cell cycle/Regulation | 3.90E−01 | 42 | 1.21 | Up |
| ITGB5 | Cell adhesion/Chemotaxis | 7.85E−01 | 17 | 1.12 | Up |
| JUN | Cell adhesion/Chemotaxis | 5.61E−01 | 23 | 1.10 | Down |
| MAP2K3 | Differentiation/Structure | 9.89E−02 | 170 | 1.09 | Up |
| MSL1 | Differentiation/Structure | 9.60E−01 | 8 | 1.01 | Down |
| NME1 | Immune Response/Inflammation/Chemotaxis | 7.39E−01 | 12 | 1.02 | Up |
| RHOC | Ion transport | 2.02E−01 | 91 | 1.11 | Down |
| CXCL11 | Immune Response/Inflammation/Chemotaxis | 3.20E−01 | 48 | 1.23 | Down |

Biomarker gene expression levels were analyzed also across the following sample sub-groups: control, adenoma between 1-2 cm, adenoma>2 cm and 4 carcinoma stages (stage I, II, III, IV), A clear over expression trend during disease evolution was observed for: IL1B, PTGS2, LTF, MMP9, S100A8, CXCL10 and CCR1, (FIG. 1), confirming their potential as biomarkers able to discriminate between carcinoma- and adenoma-bearing patients and control subjects As expected, the reference genes did not show any trend during disease evolution.

These analyses together with logistic regression analysis results allowed us to prioritize the 29 biomarkers (Table 6) and to define a group of core "indispensible" biomarkers composed of PTGS2 and IL1B, and a group of high priority markers composed of S100A8, LTF, CXCL10 and CACNB4.

TABLE 6

Prioritized list of the 29 CRC biomarkers.

| Gene | Level of Importance |
|---|---|
| IL1B | 1 |
| PTGS2 | 1 |
| S100A8 | 2 |
| LTF | 2 |
| CXCL10 | 2 |
| CACNB4 | 2 |
| MMP9 | 3 |
| CXCL11 | 3 |
| EGR1 | 3 |
| JUN | 3 |
| TNFSF13B | 3 |
| GATA2 | 3 |
| MMP11 | 3 |
| NME1 | 3 |
| PTGES | 3 |
| CCR1 | 3 |
| CXCR3 | 3 |
| FXYD5 | 3 |
| IL8 | 3 |
| ITGA2 | 3 |
| ITGB5 | 3 |
| MAPK6 | 3 |
| RHOC | 3 |
| BCL3 | 4 |
| CD63 | 4 |
| CES1 | 4 |

TABLE 6-continued

Prioritized list of the 29 CRC biomarkers.

| Gene | Level of Importance |
|---|---|
| MAP2K3 | 4 |
| MSL1 | 4 |
| PPARG | 4 |

Predictive Classifiers for Colorectal Tumour Detection

The training set containing data derived from the all 29 biomarkers was used to fit penalized logistic regression models independently for each of the following hypotheses:
  Controls versus Adenomas≥1 cm and CRC (POLCRC subset)
  Controls versus CRC (CRC subset)
  Controls versus Adenomas≥1 cm (POL subset)
  Controls versus CRC (stage I, II) (CRCI-II subset)

Penalized logistic regression models were validated directly on the training set or by non-overlapped bootstrap method: 1000 random datasets were drawn with replacement from training set; each dataset had the same size as the training set. The model was re-fit at each bootstrap and validated with the out-of-bag samples. The specificity and sensitivity average values over 1000 bootstraps were calculated at the indicated probability score cut-off and reported in Table 7. Different models are defined by different biomarker combinations.

Figure 2:
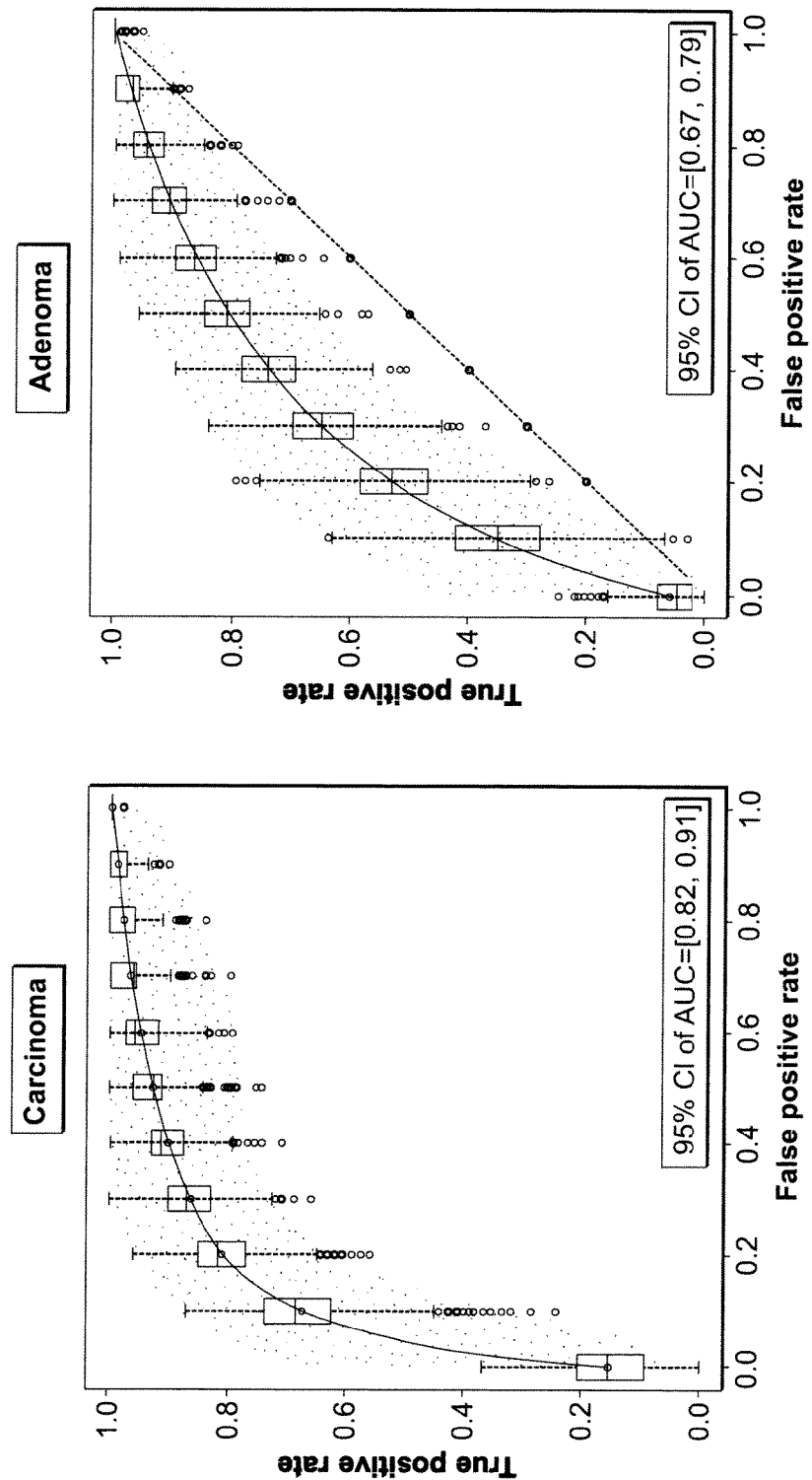
FIG. 2. Representative graphs of Receiver Operating Characteristic (ROC) curves for colorectal carcinoma (left panel) or adenoma (right panel) prediction model performances. The AUC with 95% CI are 0.82-0.91 and 0.67-0.79 for carcinoma or adenoma prediction model respectively. 1000 random datasets were drawn with replacement from training set (bootstrap); each bootstrap had the same size as the training set. At each iteration, the models are fitted and the out-of bag samples (not selected in each bootstrap) were used to validated these models. The average values over 1000 bootstraps for true positive and false positive rate are represented by the curves.
Figure 3:
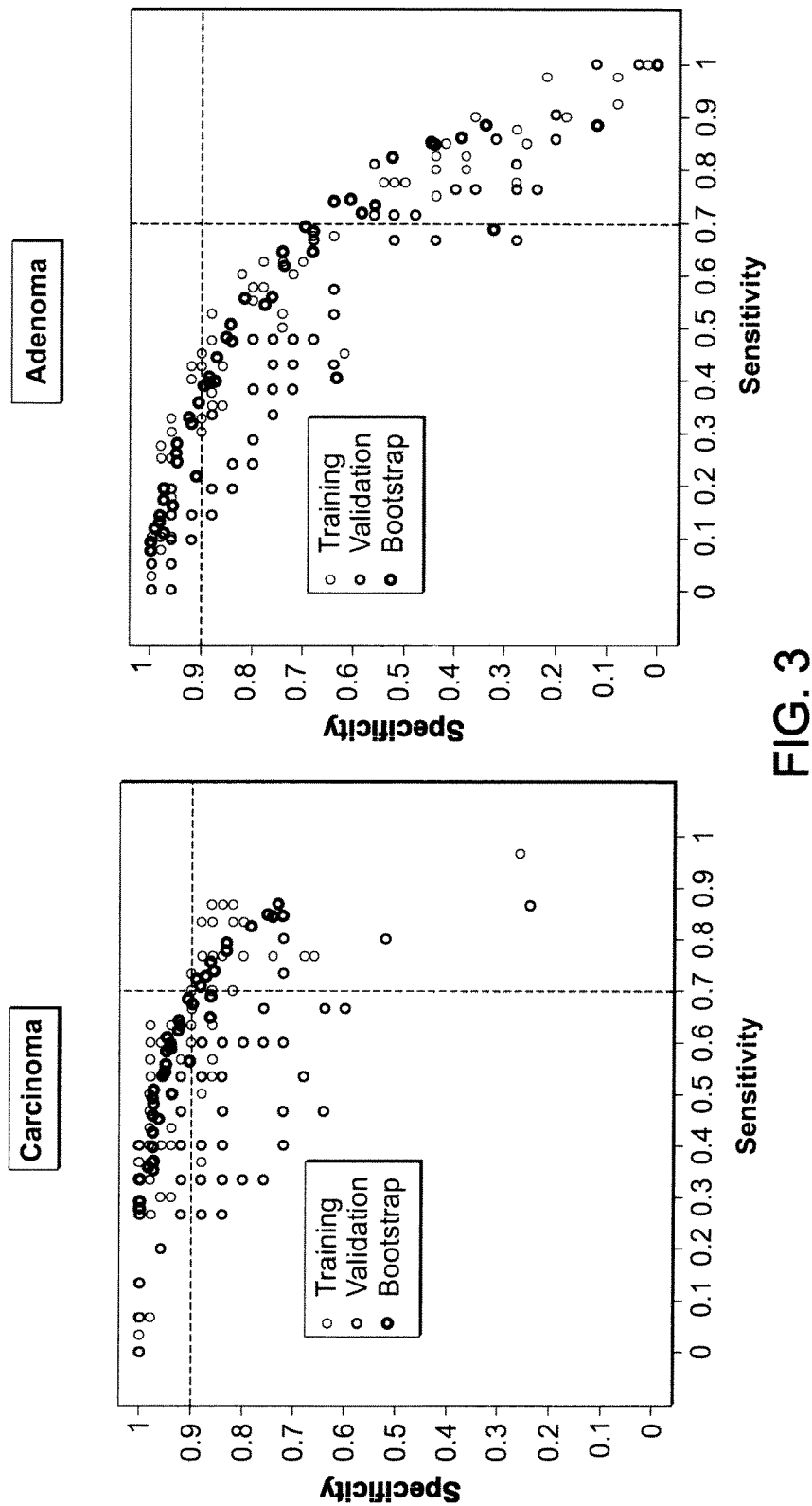
FIG. 3. Scatterplots of specificity and sensitivity for all carcinoma or adenoma prediction models calculated on the training set (blue), by bootstrap (green), or on the independent validation set (red).

Specificity and sensitivity at different probability score cut-offs were calculated and Receiver Operating Characteristics (ROC) curves generated (FIG. 2).

TABLE 7

Table summarizing the specificity and sensitivity of different statistical models obtained by bootstrap on the training set. Modelling and performances were calculated with data subset indicated and at the given probability score cut-off.
Bootstrap validation

| Model | Subset | Cutoff | Sens. | Sp. |
|---|---|---|---|---|
| GLMpath NF | CRCI-II | 0.30 | 0.70 | 0.93 |
|  | CRC | 0.50 | 0.69 | 0.90 |
|  | POLCRC | 0.75 | 0.54 | 0.85 |
|  | POL | 0.65 | 0.51 | 0.84 |
| GLMnet Alpha0.5 | CRCI-II | 0.30 | 0.76 | 0.92 |
|  | CRC | 0.5 | 0.73 | 0.89 |
|  | POLCRC | 0.75 | 0.49 | 0.88 |
|  | POL | 0.6 | 0.48 | 0.85 |
| GLMnet Alpha0.6 | CRCI-II | 0.30 | 0.75 | 0.92 |
|  | CRC | 0.5 | 0.72 | 0.89 |
|  | POLCRC | 0.75 | 0.49 | 0.88 |
|  | POL | 0.6 | 0.48 | 0.85 |
| GLMnet Alpha0.8 | CRCI-II | 0.30 | 0.74 | 0.92 |
|  | CRC | 0.5 | 0.71 | 0.88 |
|  | POLCRC | 0.75 | 0.49 | 0.87 |
|  | POL | 0.6 | 0.47 | 0.84 |
| PenalizedL1 | CRCI-II | 0.30 | 0.73 | 0.91 |
|  | CRC | 0.5 | 0.72 | 0.89 |
|  | POLCRC | 0.75 | 0.49 | 0.89 |
|  | POL | 0.6 | 0.40 | 0.87 |
| PenalizedL1L2 | CRCI-II | 0.30 | 0.72 | 0.92 |
|  | CRC | 0.5 | 0.68 | 0.90 |
|  | POLCRC | 0.70 | 0.53 | 0.87 |
|  | POL | 0.6 | 0.36 | 0.91 |

All fitted models were tested on a small independent validation set.

Best performing models were selected according to the following criteria:
1. Performance. The classifiers were selected according to the best performance in training set and validation set. To evaluate the classifier performances the sum of specificity and sensitivity was used as ranking parameter.
2. Stability. Stable classifiers across training set and validation set were defined as the ones showing the minimum of two-dimension Euclidean distance calculated between sensitivity and specificity of training set and validation set.

The Euclidean distance in 2 dimensions is given by:

$$p=(x_1,y_1)$$

$$q=(x_2,y_2)$$

$$\text{EuclideanDistance}(p,q)=\sqrt{(x_1-x_2)^2+(y_1-y_2)^2}$$

The parameters x and y are replaced by the model sensitivity and specificity on training set and validation set.

$$p=(\text{SENSI}_{TS},\text{SPECI}_{TS})$$

$$q=(\text{SENSI}_{VS},\text{SENSI}_{VS})$$

Based on the criteria explained above, two penalized logistic regression models were selected as the best performing ones: one for the detection of adenoma≥1 cm and one for the detection of colorectal carcinoma.

The adenoma predictive model equation is:

$$\log\left(\frac{Pr(y_i = 1)}{1 - Pr(y_i = 1)}\right) = -0.668 + 0.07 \times BCL3 + 0.449 \times CACNB4 -$$
$$0.274 \times CCR1 + 0.174 \times CXCL10 - 0.260 \times IL1B - 0.115 \times ITGA2 -$$
$$0.083 \times ITGB5 - 0.130 \times LTF - 0.024 \times MAP2K3 -$$
$$0.213 \times MAPK6 + 0.297 \times MMP11 + 0.001 \times PTGES -$$
$$0.140 \times PTGS2 - 0.145 \times S100A8 - 0.212 \times TNFSF13B$$

The carcinoma predictive model equation is:

$$\log\left(\frac{Pr(y_i = 1)}{1 - Pr(y_i = 1)}\right) = -8.544 + 0.707 \times CACNB4 +$$
$$0.688 \times CXCL10 - 0.592 \times IL1B - 0.234 \times LTF + 0.044 \times MMP11 +$$
$$0.105 \times PTGES - 0.143 \times PTGS2 - 1.605 \times S100A8$$

The CRC predictive model showed, for CRC detection, a specificity of 92% and sensitivity of 67% when it was applied to the training set itself without bootstrap and a specificity of 84% and sensitivity of 60% when it was applied to the independent validation set. On the other side, the adenoma predictive model showed, for adenoma≥1 cm detection, a specificity of 88% and sensitivity of 50% when it was applied to the training set itself without bootstrap and a specificity of 76% and sensitivity of 47% when it was applied to the independent validation set.

Other predictive models, defined by different biomarker combinations, together with their diagnostic accuracy are reported in Table 8 and Table 9.

TABLE 8

Penalized logistic regression models.

| Equation # | 1 | 2 | 3 | 4 | 5 |
|---|---|---|---|---|---|
| Intercept $\beta_0$ | −0.393 | 4.353 | 2.195 | 5.722 | 4.571 |
| IL1B | −0.068 | −0.386 | −0.238 | −0.339 | −0.379 |

TABLE 8-continued

Penalized logistic regression models.

| Equation # | 1 | 2 | 3 | 4 | 5 |
|---|---|---|---|---|---|
| PTGS2 | 0 | −0.061 | −0.224 | −0.182 | −0.080 |
| S100A8 | −0.668 | 0 | −1.447 | −1.445 | −0.037 |
| LTF | 0.000 | −0.120 | 0 | −0.292 | −0.131 |

The table reports the corresponding β coefficients that define the fitted logistic equations. Logistic equation has the form:

$$\log\left(\frac{Pr(y_i = 1)}{1 - Pr(y_i = 1)}\right) = \beta_0 + \beta_1 x_{1,i} + \ldots + \beta_m x_{m,i}$$

where $x_{m,i}$ is a measured value for the biomarker m and subject i and $(\beta_0, \beta_1, \ldots, \beta_m)$ is a vector of coefficients. A coefficient equal to 0 means that the biomarker is not considered by the model.

TABLE 9

Sensitivity and specificity for CRC and adenoma (POL) detection of the predictive models reported in Table 8.

| Equation # | Biomarker combination | Training Set | | | Validation Set | | |
|---|---|---|---|---|---|---|---|
| | | Sp | Sn CRC | Sn POL | Sp | Sn CRC | Sn POL |
| 1 | IL1B, S100A8 | 0.80 | 0.60 | 0.43 | 0.88 | 0.53 | 0.33 |
| 2 | IL1B, PTGS2, LTF | 0.94 | 0.47 | 0.35 | 0.80 | 0.27 | 0.33 |
| 3 | IL1B, PTGS2, S100A8 | 0.88 | 0.57 | 0.33 | 0.92 | 0.47 | 0.29 |
| 4 | IL1B, PTGS2, S100A8, LTF | 0.92 | 0.60 | 0.30 | 0.80 | 0.47 | 0.33 |
| 5 | IL1B, PTGS2, S100A8, LTF | 0.94 | 0.47 | 0.40 | 0.80 | 0.27 | 0.33 |

What is claimed is:

1. A method for detecting IL1B, PTGS2 and at least one of S100A8, LTF, CXCL10, and CACNB4, the method comprising:
   (a) extracting RNA from blood cells in peripheral blood from a selected subject to produce extracted RNA; and
   (b) measuring in the extracted RNA the amount of mRNA for each biomarker in one biomarker panel, wherein the biomarker panel consists of from 3 to 29 biomarkers, wherein the 3 to 29 biomarkers comprise IL1B, PTGS2, and at least one of S100A8, LTF, CXCL10, and CACNB4,
   wherein said method does not comprise measuring more than 29 biomarkers.

2. The method of claim 1, wherein the subject has a history of colorectal polyps.

3. The method of claim 1, wherein the subject has ulcerative colitis or Crohn's disease.

4. The method of claim 1, wherein the subject is obese.

5. The method of claim 1, wherein the subject has a history of colorectal cancer.

6. The method of claim 1, wherein the subject has inflammatory bowel disease.

7. The method of claim 1, wherein the subject has had a positive fecal occult blood test.

8. The method of claim 1, wherein the subject does not have a history of colorectal polyps.

9. The method of claim 1, wherein the subject does not have a history of cancer.

10. The method of claim 1, wherein the subject has diabetes.

11. The method of claim 1, wherein the subject is at least 50 years old and has not been previously diagnosed or identified as having a colorectal tumor.

12. The method of claim 1, wherein the subject has as familial adenomatous polyposis (FAP), hereditary non-polyposis colon cancer (HNPCC), Turcot syndrome, Peuz-Jegher syndrome, or MUTYH-associated polyposis.

13. The method of claim 1, wherein the 3 to 29 biomarkers further comprise MMP9, CXCL11, EGR1, JUN, TNFSF13B, GATA2, MMP11, NME1, PTGES, CCR1, CXCR3, FXYD5, IL8, ITGA2, ITGB5, MAPK6, RHOC, BCL3, CD63, CES1, MAP2K3, MSL1, or PPARG.

14. The method of claim 13, wherein the 3 to 29 biomarkers consist of IL1B, PTGS2, S100A8, LTF, CXCL10, CACNB4, MMP9, CXCL11, EGR1, JUN, TNFSF13B, GATA2, MMP11, NME1, PTGES, CCR1, CXCR3, FXYD5, IL8, ITGA2, ITGB5, MAPK6, RHOC, BCL3, CD63, CES1, MAP2K3, MSL1, and PPARG.

15. A method for detecting IL1B, PTGS2 and at least one of S100A8, LTF, CXCL10, and CACNB4, the method comprising:
   (a) extracting RNA from blood cells in peripheral blood from a selected subject to produce extracted RNA; and
   (b) measuring in the extracted RNA the amount of mRNA for each biomarker in a biomarker panel, wherein the biomarker panel comprises the biomarkers IL1B, PTGS2, and at least one of S100A8, LTF, CXCL10, and CACNB4,
   wherein the subject is at least 50 years old and has not been previously diagnosed or identified as having a colorectal tumor,
   wherein said method does not comprise measuring more than 29 biomarkers.

16. The method of claim 15, wherein the subject has a history of colorectal polyps.

17. The method of claim 15, wherein the subject has ulcerative colitis or Crohn's disease.

18. The method of claim 15, wherein the subject is obese.

19. The method of claim 15, wherein the subject has inflammatory bowel disease.

20. The method of claim 15, wherein the subject has had a positive fecal occult blood test.

21. The method of claim 15, wherein the subject does not have a history of colorectal polyps.

22. The method of claim 15, wherein the subject does not have a history of cancer.

23. The method of claim 15, wherein the subject has diabetes.

24. The method of claim 15, wherein the subject has familial adenomatous polyposis (FAP), hereditary non-polyposis colon cancer (HNPCC), Turcot syndrome, Peuz-Jegher syndrome, or MUTYH-associated polyposis.

* * * * *